United States Patent [19]

Stahly

[11] Patent Number: 4,502,996

[45] Date of Patent: Mar. 5, 1985

[54] NUCLEOPHILIC SUBSTITUTION PROCESS

[75] Inventor: G. Patrick Stahly, Baton Rouge, La.

[73] Assignee: Ethyl Corporation, Richmond, Va.

[21] Appl. No.: 452,615

[22] Filed: Dec. 23, 1982

Related U.S. Application Data

[63] Continuation-in-part of Ser. No. 418,915, Sep. 16, 1982, abandoned, which is a continuation-in-part of Ser. No. 317,322, Nov. 2, 1981, abandoned.

[51] Int. Cl.$^3$ ............................................ C07C 121/50
[52] U.S. Cl. .................................................. 260/465 G
[58] Field of Search .................................... 260/465 G

[56] References Cited

PUBLICATIONS

Golinski et al., Tetrahedron Letter No. 37, pp. 3495–3498 (1978).

Makosza et al., J. Org. Chem., vol. 45, pp. 1534–1535 (1980).

Mokosza, Int. Conf. Chem. Biotechol. Biol. Act. Nat. Prod. (Proc.), vol. 2, pp. 480–490 (1981).

Primary Examiner—Delbert R. Phillips
Attorney, Agent, or Firm—Donald L. Johnson; John F. Sieberth; Patricia J. Hogan

[57] ABSTRACT

Halonitroarylacetonitriles are prepared by reacting a halonitroaromatic compound wherein the halo substituent has an atomic number of at least 17 with an alpha,alpha-disubstituted acetonitrile in an inert solvent and in the presence of a base so that the nitrile undergoes a nucleophilic substitution on an unsubstituted ring carbon of the halonitroaromatic compound during which an alpha-substituent functions as a leaving group. The halonitroarylacetonitriles formed by the process can be readily converted into derivatives, such as pharmaceuticals.

12 Claims, No Drawings

NUCLEOPHILIC SUBSTITUTION PROCESS

CROSS-REFERENCE

This application is a continuation-in-part of copending application Ser. No. 418,915, filed Sept. 16, 1982, which in turn is a continuation-in-part of application Ser. No. 317,322, filed Nov. 2, 1981, both abandoned.

TECHNICAL FIELD

This invention relates to halonitroarylacetonitriles and derivatives thereof—more particularly to processes for preparing the nitriles and derivatives.

BACKGROUND

As demonstrated by U.S. Pat. No. 4,239,901 (Rainer) and Carney et al., "A Potent Non-Steroidal Anti-Inflammatory Agent: 2-[3-Chloro-4-(3-pyrrolinyl)-phenyl]propionic Acid," *Experientia*, Vol. 29, page 938 (1973), it is known that chloronitrobenzene acetic acids and derivatives thereof are particularly useful intermediates for the synthesis of pharmaceuticals. Carney et al. show the utility of ethyl 2-(3-chloro-4-nitrobenzene)-propionate in this regard, and Rainer teaches that polychloronitrobenzeneacetic acid esters are among the intermediates that can be used to prepare his pyrazol-1-ylphenylacetic acid and pyrazolinl-ylphenylacetic acid anti-inflammatory agents.

In the past, a disadvantage of employing chloronitrobenzeneacetic acids or esters, or the corresponding chloroaminobenzeneacetic acids or esters, as pharmaceutical intermediates has been the difficulty of preparing those intermediates by conventional techniques. Even the preferred procedures for preparing such compounds have proven to be tedious, difficult, and time-consuming operations. For example, as indicated in the Carney et al. article and in Example 23 of U.S. Pat. No. 3,868,391 (Carney et al. II), the conventional method of synthesizing esters of chloronitrobenzene or chloroaminobenzene alpha-methylacetic acids involves (1) alkylating a suitable polychloronitrobenzene with the diethyl ester of methylmalonic acid in the presence of a strong base, such as sodium hydride, and a suitable solvent, such as N,N-dimethylformamide or hexamethylphosphoramide, to form an ester of chloronitrophenyl-2-methylmalonic acid, (2) reducing the nitro group to an amino group when an amino compound is desired, and (3) subjecting the ester of the chloronitrophenyl or chloroaminophenyl-2-methylmalonic acid to hydrolysis, decarboxylation, and re-esterification—a reaction sequence that involved almost two days of refluxing in Example 23 of Carney et al. II. In a similar procedure found in his Example 16, Rainer's hydrolysis/decarboxylation step was conducted under reflux for five days.

Obviously, it would be a welcome contribution to the art to provide a method of synthesizing materials such as the aforementioned pharmaceuticals in a simple and straightforward manner without a need for the tedious and time-consuming operations associated with the conventional process approach.

SUMMARY OF THE INVENTION

An object of this invention is to provide novel processes for preparing halonitroarylacetonitriles.

Another object is to provide such processes which permit the preparation of the nitriles in good yield with high selectivity in a very simple and straightforward manner.

A further object is to provide novel, improved processes for preparing derivatives of halonitroarylacetonitriles.

These and other objects are attained by (A) reacting a halonitroaromatic compound wherein the halo substituent has an atomic number of at least 17 with an alpha,alpha-disubstituted acetonitrile in an inert solvent and in the presence of a base so that the nitrile undergoes a nucleophilic substitution on an unsubstituted ring carbon of the halonitroaromatic compound during which an alpha-substituent functions as a leaving group, thereby forming a halonitroarylacetic acid ester, and (B) when appropriate, converting the halonitroarylacetonitrile to a desired derivative thereof.

DETAILED DESCRIPTION

Halonitroaromatic compounds utilizable in the practice of the invention include a variety of such compounds—the chief requirements for their utility being that (1) they bear at least one ar-nitro and at least one ar-halo substituent, (2) their halo substituents be selected from halo substituents that would be expected to be somewhat resistant to being displaced by the nucleophile under the conditions of the reaction, i.e., chloro, bromo, and iodo substituents, (3) they contain at least one replaceable hydrogen on an aromatic ring to which a nitro group is attached, and (4) they be devoid of substituents which would interfere with the desired nucleophilic substitution reaction.

Thus, the utilizable halonitroaromatic compounds include compounds having one or more simple of fused aromatic rings containing five or six members and either bearing no substituents other than nitro and halo substituents or also bearing any of a variety of inert substituents, i.e., substituents that do not interfere with the desired nucleophilic substitution reaction, such as alkyl, alkoxy, alkylmercapto, trifluoromethyl, dialkylamino, dialkanoylamino, cyano, dialkylcarbamoyl, alkylsulfonyl, dialkylsulfamoyl, alkoxyalkyl, haloalkyl, cycloalkyl, halocycloalkyl, etc.—any alkyl chains in the substituents generally being lower alkyl chains. ("Lower alkyl" is used in this specification in its usual sense to refer to an alkyl group containing up to about 6 carbons.) When the halonitroaromatic compound contains more than one ring, any such inert substituent may be on the same ring as the ring bearing the halo and nitro substituents and/or on a ring which is directly or indirectly attached to the ring bearing the halo and nitro substituents.

When the aromatic ring bearing the halo and nitro substituents is a six-membered ring, there will be at least one replaceable hydrogen in a position para or ortho to the carbon bearing the nitro substituent; and it is preferred that there be a replaceable hydrogen in the para position. Halonitroaromatic compounds having a five-membered ring should have a replaceable hydrogen on a carbon adjacent to, or separated by two ring atoms from, the carbon bearing the nitro substituent.

Exemplary of halonitroaromatic compounds that may be used in the practice of the invention are the 2-, 3-, and 4-chloronitrobenzenes; the 2,3-, 2,4-, 2,5-, 2,6-, 3,4-, and 3,5-dichloronitrobenzenes; the various trichloronitrobenzenes; the corresponding bromo and iodo compounds; the various dimethyl-, diethyl-, and dibutylnitrobenzenes, nitrobiphenyls, benzylnitrobenzenes, nitronaphthalenes, di- and trinitrobenzenes, nitro-N,N-diethylanilines, nitrodiphenyl esters, nitro-N-ethylacetanilides, nitrobenzylcyanides, nitrophenyl acetates, nitropyridine-N-oxides, nitroquinolines, nitroisoquinolines, nitrothiophenes, and the like bearing one or more ar-chloro, bromo, or iodo substituents and containing at least one replaceable hydrogen in an appropriate position.

Since it has been found that iodo substituents tend to be removed under the conditions of the substitution reaction, the preferred halonitroaromatic compounds are those in which the halo substituents are chloro or bromo, most preferably chloro.

In some cases, polynitroaromatic reactants may undergo substitution reactions whereby one of the nitro groups is replaced by the nitrile reactant. Therefore, the possibility of this competitive reaction should be kept in mind when selecting a polynitroaromatic for use in the process.

The preferred halonitroaromatic compounds are mononuclear halonitroaromatic compounds, especially halonitrobenzenes. Particularly preferred halonitroaromatic compounds are the halonitrobenzenes having a replaceable hydrogen in the position para to the nitro group, since the nucleophilic substitution reaction of the invention tends to be highly selective on the para position, and the use of such compounds therefore leads to the production of halonitrobenzeneacetic acid esters which are ideally suited for the synthesis of anti-inflammatory agents of the type described in the aforementioned references. Even more preferred are such halonitrobenzenes having a halo substituent in a position ortho to the nitro group. A halonitrobenzene which is especially preferred is 2-chloronitrobenzene, which is readily converted with high selectivity into such products as 2-[3-chloro-4-(3-pyrrolinyl)phenyl]propionic acid and related anti-inflammatory agents.

The alpha,alpha-disubstituted acetonitriles that can be used in the practice of the invention also include a variety of such compounds, which—in general—may be represented by the formula:

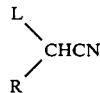

wherein L is a leaving group and R is halo (preferably chloro) or, more preferably, a hydrocarbyl (e.g., alkyl, alkenyl, alkynyl, cycloalkyl, cycloalkenyl, aryl, aralkyl, etc.) or hydrocarbyloxyhydrocarbyl (e.g., alkoxyalkyl, aryloxyalkyl, alkoxyaryl, alkoxycycloalkyl, etc.) group which most preferably contains up to about 10 carbons.

Exemplary leaving groups, L, include halo, aryloxy, haloaryloxy, alkylthio, cycloalkylthio, arylthio, aralkylthio, haloalkylthio, halocycloalkylthio, haloarylthio, haloaralkylthio, or, less preferably, alkoxy, cycloalkoxy, aralkoxy, haloalkoxy, halocycloalkoxy, haloaralkoxy, and the like, as well as other suitable leaving groups which have been described in the literature, e.g., in Golinski et al., "'Vicarious' Nucleophilic Substitution of Hydrogen in Aromatic Nitro Compounds," *Tetrahedron Letters*, Vol. 37, pp. 3495–8 (1978) and in Makosza et al., "Vicarious Substitution of Hydrogen in Aromatic Nitro Compounds with Acetonitrile Derivatives," *Journal of Organic Chemistry*, Vol. 45, pp. 1534–5 (1980).

When the leaving group is an organic group, it is generally preferred that it contain not more than about 10 carbons, although organic leaving groups having an even higher carbon content are satisfactory in the practice of the invention. Preferably, the leaving group is halo, i.e., chloro, bromo, fluoro, or iodo; and it is more preferably chloro or bromo, most preferably chloro.

A few examples of alpha,alpha-disubstituted acetonitriles that can be used in the practice of the invention are 2-chloropropionitrile, 2-chlorobutyronitrile, 2-chlorovaleronitrile, 2-chlorocapronitrile, 2-chloro-4-pentenenitrile, 2-chloro-3,3-dimethylbutyronitrile, 2-chloro-2-phenylacetonitrile, 2-chloro-2-cyclohexylacetonitrile, 2-chloro-3-(3-chloro-o-tolyl)propionitrile, 2-chloro-3-phenylpropionitrile, the corresponding bromo and iodo compounds, and the like. The alpha-halo-alpha-hydrocarbylacetonitriles, i.e., alpha-haloalkyl cyanides containing at least three carbons—particularly 2-chloropropionitrile and 2-bromopropionitrile—are especially preferred, although similar cyanides in which the alpha-halo substituent is replaced by one of the other leaving groups mentioned above are also highly desirable.

In another highly desirable embodiment of the invention, the alpha,alpha-disubstituted acetonitrile is an alpha,alpha-dihaloacetonitrile, most preferably an alpha,alpha-dichloroacetonitrile, which leads to the formation of a product having a reactive halo substituent in the alpha-position, e.g., a product corresponding to the formula:

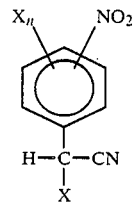

wherein X is halo, preferably chloro, and n is an integer of at least 1. Such products enable facile synthesis of a variety of end products. Most preferably the nitro group is in the position para to the nitrile substituent, although it may be located in an ortho position.

It is to be noted that attempts to employ chloroacetonitrile in the process of this invention have been unsuccessful thus far. No reaction was detected when an attempt was made to react chloroacetonitrile with 2-chloronitrobenzene in the presence of sodium hydride in N,N-dimethylformamide. In this connection, it is interesting to note the results reported in the aforementioned Makosza et al article, viz., the success in reacting chloroacetonitrile with 1-nitronaphthalene and 4-chloronitrobenzene in the presence of sodium hydroxide in dimethylsulfoxide to form the corresponding alpha-nitroarylacetonitriles vs. the lack of success in obtaining a substitution product from nitrobenzene.

The solvent used in a nucleophilic substitution process of the invention may be any solvent that is inert under the conditions of the reaction, i.e., any solvent that will not prevent the reaction from occurring. Such solvents are substantially anhydrous and are generally aprotic, although solvents such as liquid ammonia are also utilizable.

Illustrative aprotic solvents which may be employed in the process of the invention include ethers such as diethyl ether, 1,3-dioxolane, diglyme, 1,2-diethoxyethane, anisole, etc.; tertiary amines such as pyridine, N-ethylpiperidine, triethyl amine, tributyl amine, N,N-diphenyl-N-methyl amine, N,N-dimethylaniline, etc.; and other aprotic solvents. However, the preferred aprotic solvents are dipolar aprotic solvents such as dimethyl sulfoxide, N,N-dimethylformamide, N,N-dimethylacetamide, dimethyl sulfone, tetramethylene sulfone, N-methylpyrrolidinone, and the like.

Bases useful in the practice of the invention include all bases strong enough to activate the nitrile reactant, e.g., alkaline earth metal compounds such as calcium oxide, calcium hydride, calcium hydroxide, barium oxide, barium hydroxide, magnesium hydroxide, zinc hydroxide, etc. However, the base is preferably an alkali metal compound, e.g., an organoalkali metal compound, alkali metal hydride, alkali metal hydroxide, alkali metal oxide, alkali metal amide, or alkali metal alcoholate, such as butyllithium, phenyllithium, ethylsodium, amylsodium, butylpotassium, benzylpotassium, sodium dimsylate (i.e., the sodium salt of diethylsulfoxide), sodium hydride, potassium hydride, sodium hydroxide, potassium hydroxide, sodium oxide, potassium oxide, sodium amide, potassium amide, lithium diisopropylamide, sodium methoxide, potassium t-butoxide, the sodium salt of the monomethylether of ethylene glycol, sodium phenoxide, and the like. Ordinarily the use of sodium hydride or potassium hydride will be found most convenient and economical.

Use of an alkali metal compound as the base permits the alternatives of using the alkali metal compound alone or in conjunction with a phase transfer catalyst, such as a quaternary ammonium salt, ethylene glycol, or a suitable crown ether. When a phase transfer catalyst is employed (1) the alkali metal compound may be any of the alkali metal compounds generally or specifically indicated above, although the type of alkali metal compound being used determines the type of crown ether that is preferably utilized—lithium bases generally calling for the use of a 12-crown-4 ether, sodium bases generally calling for the use of a 15-crown-5 ether, and potassium bases generally calling for the use of an 18-crown-6 ether, and (2) the reaction medium may be any of the aprotic solvents mentioned above, or it may be an inert liquid hydrocarbon such as benzene, toluene, xylene, hexane, heptane, isooctane, or the like.

When an alkali metal hydride, especially a highly pure alkali metal hydride, is employed as the base, it is desirable to include a small amount of a transfer agent such as water, alcohol, or the like in the system. It is believed that the transfer agent activates the hydride by reacting therewith to form a small amount of the alkali metal hydroxide or alcoholate.

The halonitroarylacetonitrile synthesis of the invention is conducted in a substantially anhydrous reaction system, and accordingly, except when a small amount of water (which is itself consumed by reaction with the alkali metal hydride) is employed as a transfer agent, the components of the reaction system should be brought together and maintained under a dry inert atmosphere. Thus, while it is possible to conduct the process in the presence of air, it is desirable to maintain the reaction system under an atmosphere of dry nitrogen or the like. Since the reaction itself is normally an exothermic reaction, with its initiation readily ascertainable by noting the exotherm produced, the reactants are ordinarily brought together at ambient temperatures, although the temperature may be raised or lowered to suit the needs of the occasion if desired.

The halonitroaromatic compound and alpha,alpha-disubstituted acetonitrile may be used in amounts such as to provide a stoichiometric excess of either of the reactants or the stoichiometric amount of each. However, when a stoichiometric excess of the halonitroaromatic compound is employed, the quantity of product obtainable will be limited by the quantity of nitrile used, so it is desirable to utilize a stoichiometric excess of the nitrile. The amount of base employed is preferably such as to provide at least two molar equivalents of base per mole of halonitroaromatic compound, since the use of smaller amounts—although permitting the reaction to occur—makes the base the limiting reagent.

The mode of addition of the ingredients of the reaction system is not particularly critical. Accordingly, it is convenient to add the halonitroaromatic compound to a mixture of the other materials, add the base to a mixture of the other materials, add the reactants to a mixture of the base and inert solvent, introduce all four ingredients simultaneously into the reaction zone, or the like. Since the reaction ordinarily proceeds very rapidly, long reaction times are not required. The reaction will usually be completed within a matter of minutes or a few hours at ambient temperatures.

When derivatives of the halonitroarylacetonitriles are desired, they may be prepared by employing conventional techniques to convert to the desired derivatives the halonitroarylacetonitriles made in accordance with the present invention. Thus, for example:

(A) 2-(3-chloro-4-nitrobenzene)propionitrile synthesized by the process of this invention may be selectively hydrogenated to 2-(4-amino-3-chlorobenzene)propionitrile, which in turn may be reacted with a 1,4-dihalo-2-butene (e.g., 1,4-dibromo-2-butene or 1,4-dichloro-2-butene, preferably cis-1,4-dichloro-2-butene) to form 2-[3-chloro-4-(3-pyrrolinyl)phenyl]propionitrile, which may be hydrolyzed to 2-[3-chloro-4-(3-pyrrolinyl)phenyl]propionic acid, (B) 2-(3-chloro-4-nitrobenzene)propionitrile synthesized by the process of this invention may be selectively hydrogenated and hydrolyzed (in either order) to form 2-(4-amino-3-chlorobenzene)propionic acid, which in turn may be esterified and reacted with a 1,4-dihalo-2-butene to form a 2-[3-chloro-4-(3-pyrrolinyl)phenyl]propionate, which may be hydrolyzed to the free acid, (C) 2-(3-chloro-4-nitrobenzene)propionitrile synthesized by the process of this invention may be hydrogenated to 2-(4-aminobenzene)propionitrile, which in turn may be reacted with phthalic anhydride to form 2-(4-phthalimidophenyl)propionitrile, which may be reduced and hydrolyzed to 2-[4-(1,3-dihydro-1-oxo-2H-isoindol-2-yl)phenyl]propionic acid, (D) 2-(3-chloro-4-nitrobenzene)propionitrile synthesized by the process of this invention may be hydrolyzed to 2-(3-chloro-4-nitrobenzene)propionic acid, which in turn may be reduced to 2-(4-aminobenzene)propionic acid, reacted with phthalic anhydride to form 2-(4-phthalimidophenyl)propionic acid, and reduced to 2-[4-(1,3-dihydro-1-oxo-2H-isoindol-2-yl)phenyl]propionic acid, and (E) 2-(3-chloro-4-nitrobenzene)propionitrile isomers and analogs synthesized by the process of this invention may be subjected to similar reactions.

The particular conventional techniques used to convert the halonitroarylacetonitriles into their various derivatives are not critical. It may sometimes be desirable to use certain particular techniques for the preparation of the derivatives, e.g., the reduction, hydrolysis, and cyclization techniques taught in Carney et al.; March, *Advanced Organic Chemistry*, McGraw-Hill, New York (1977), pp. 809-10, and 1125-6; the references cited therein; U.S. Pat. Nos. 3,641,040 and 3,997,669; Swiss Pat. Nos. 574,921–574,926; and German Offenlegungsschriften Nos. 19 21 654 and 20 12 327, the disclosures of all of which are incorporated herein by reference. However, the overall processes for preparing the derivatives are simplified and made more efficient and economical by the present simplification of the synthesis of the halonitroarylacetonitriles, regardless of the particular techniques used to convert them into their various derivatives.

As indicated above, the present invention is particularly advantageous in providing a readier and more economical route to the synthesis of pharmaceuticals and other chemical products that can be prepared from halonitroarylacetonitriles. Such products include, not only those mentioned above, but a variety of products, such as products disclosed in U.S. Pat. Nos. 3,641,040, 3,657,230, 3,767,805, 3,868,391, 3,936,467, 3,993,763, 3,997,669, 4,010,274, 4,118,504, 4,126,691, 4,163,788, and 4,239,901.

The following example is given to illustrate the invention and is not intended as a limitation thereof.

EXAMPLE

To a slurry of 0.50 g (10 mmols) of NaH (50% dispersion in mineral oil) in 2 ml of N,N-dimethylformamide (DMF, dried over 3 Angstrom molecular sieves) under nitrogen was added dropwise, over a period of 10 minutes, a solution of 0.60 ml (5.1 mmols) of 2-chloronitrobenzene and 0.42 ml (5.1 mmols) of 2-chloropropionitrile in 1 ml of DMF. During the addition, the mixture became purple and an exotherm was observed. The reaction mixture was stirred under nitrogen for 15 minutes, poured into 30 ml of 1N HCl and extracted with four 30 ml portions of diethyl ether. The organic layers were combined, dried using $MgSo_4$, and concentrated to give 1.2 g of a black oil. Preparative thin layer chromatography of 0.20 g of this oil (one 2 mm silica gel plate developed with 50% $CH_2Cl_2$/50% petroleum ether) afforded 0.088 gram of 2-(3-chloro-4-nitrobenzene)propionitrile which was characterized by means of NMR and mass spectrometry.

As noted above, a feature of this invention is the use of an alpha,alpha-disubstituted acetonitrile. The following Comparative Example serves to illustrate this requirement.

COMPARATIVE EXAMPLE

Into a flame-dried flask under nitrogen were placed 500 mg of a 60% slurry of sodium hydride in mineral oil. This was washed three times with 5 ml of portions of petroleum ether (b.p. 35°–60° C.), slurried in 4 ml of N,N-dimethylformamide, and cooled in an ice-water bath. One drop of a solution of 985 mg 2-chloronitrobenzene and 500 mg chloroacetonitrile in 1 ml of N,N-dimethylformamide was added to the slurry. It turned brown and then a dirty purple. After one minute, the balance of the solution was added dropwise over a five minute period, and the mixture was stirred for 15 minutes. During this time, the reaction mixture remained cool—no exotherm was noted. Then the mixture was poured into 50 ml of 1N HCl and extracted three times with 40 ml portions of diethylether. It was noted that some rag layers formed and that both the ether and aqueous layers were black. The ether layers were combined, dried ($MgSO_4$), and stirred to give 1.27 g of black oil. Thin layer chromotographic analysis and vapor phase chromotographic analysis showed only 2-chloronitrobenzene—no 2-(3-chloro-4-nitrobenzene)acetonitrile was detected.

This invention is susceptible to considerable variation within the spirit and scope of the appended claims.

I claim:

1. A process which comprises (A) reacting 2-chloronitrobenzene with an alpha-chloro- or alpha-bromopropionitrile in an inert dipolar aprotic solvent and in the presence of a strong alkali metal compound base so that the nitrile undergoes a nucleophilic substitution on an unsubstituted ring carbon of the chloronitrobenzene during which the alpha-chloro or alpha-bromo substituent functions as a leaving group, thereby forming 2-(2-chloronitrobenzene)propionitrile, and (B) selectively reducing the 2-(2-chloronitrobenzene)propionitrile to 2-(4-amino-3-chlorobenzene)propionitrile.

2. The process of claim 1 wherein the nitrile reactant is 2-chloropropionitrile.

3. The process of claim 1 wherein the solvent is N,N-dimethylformamide.

4. The process of claim 1 wherein the base is sodium hydride or potassium hydride.

5. A process which comprises (A) reacting 2-chloronitrobenzene with an alpha-chloro- or alpha-bromopropionitrile in an inert dipolar aprotic solvent and in the presence of a strong alkali metal compound base so that the nitrile undergoes a nucleophilic substitution on an unsubstituted ring carbon of the chloronitrobenzene during which the alpha-chloro or alpha-bromo substituent functions as a leaving group, thereby forming 2-(2-chloronitrobenzene)propionitrile, (B) selectively reducing the 2-(2-chloronitrobenzene)propionitrile to 2-(4-amino-3-chlorobenzene)propionitrile, and (C) reacting the 2-(4-amino-3-chlorobenzene)propionitrile with a 1,4-dihalo-2-butene to form 2-[3-chloro-4-(3-pyrrolinyl)phenyl]propionitrile.

6. The process of claim 5 wherein the nitrile reactant is 2-chloropropionitrile.

7. The process of claim 5 wherein the solvent is N,N-dimethylformamide.

8. The process of claim 5 wherein the base is sodium hydride or potassium hydride.

9. A process which comprises (A) reacting 2-chloronitrobenzene with an alpha-chloro- or alpha-bromopropionitrile in an inert dipolar aprotic solvent and in the presence of a strong alkali metal compound base so that the nitrile undergoes a nucleophilic substitution on an unsubstituted ring carbon of the chloronitrobenzene during which the alpha-chloro or alpha-bromo substituent functions as a leaving group, thereby forming 2-(2-chloronitrobenzene)propionitrile, (B) selectively reducing the 2-(2-chloronitrobenzene)propionitrile to 2-(4-amino-3-chlorobenzene)propionitrile, (C) reacting the 2-(4-amino-3-chlorobenzene)propionitrile with a 1,4-dihalo-2-butene to form 2-[3-chloro-4-(3-pyrrolinyl)phenyl]propionitrile, and (D) converting the 2-[3-chloro-4-(3-pyrrolinyl)phenyl]propionitrile to 2-[3-chloro-4-(3-pyrrolinyl)phenyl]propionic acid.

10. The process of claim 9 wherein the nitrile reactant is 2-chloropropionitrile.

11. The process of claim 9 wherein the solvent is N,N-dimethylformamide.

12. The process of claim 9 wherein the base is sodium hydride or potassium hydride.

* * * * *